US 6,740,640 B2

(12) United States Patent
Yamazaki et al.

(10) Patent No.: US 6,740,640 B2
(45) Date of Patent: May 25, 2004

(54) SULFOFUCOSYLACYLGLYCEROL DERIVATIVES AND ADMINISTRATION THEREOF AS MEDICAMENTS

(75) Inventors: Takayuki Yamazaki, Noda (JP); Fumio Sugawara, Niiza (JP); Keisuke Ohta, Noda (JP); Kazuyoshi Masaki, Sakado (JP); Kotaro Nakayama, Yotsukaido (JP); Kengo Sakaguchi, Tsukuba (JP); Noriyuki Sato, Sapporo (JP); Hiroeki Sahara, Sapporo (JP); Tatsuya Fujita, Sapporo (JP)

(73) Assignee: Toyo Suisan Kaisha, Ltd., Tokyo (JP)

( * ) Notice: Subject to any disclaimer, the term of this patent is extended or adjusted under 35 U.S.C. 154(b) by 192 days.

(21) Appl. No.: 09/939,153

(22) Filed: Aug. 24, 2001

(65) Prior Publication Data

US 2002/0028777 A1 Mar. 7, 2002

Related U.S. Application Data

(63) Continuation-in-part of application No. PCT/JP00/00974, filed on Feb. 21, 2000.

(30) Foreign Application Priority Data

Feb. 26, 1999 (JP) ............................................ 11-051398

(51) Int. Cl.$^7$ ......................... C07H 15/00; A61K 31/70
(52) U.S. Cl. ............................. 514/25; 536/54; 536/118; 536/4.1
(58) Field of Search ............................. 514/25; 536/4.1, 536/54, 118

(56) References Cited

U.S. PATENT DOCUMENTS

| | | | | |
|---|---|---|---|---|
| 5,489,578 A | * | 2/1996 | Rosen et al. | 514/61 |
| 5,695,752 A | * | 12/1997 | Rosen et al. | 424/94.61 |
| 5,783,693 A | * | 7/1998 | Bertozzi et al. | 536/124 |
| 6,395,886 B1 | * | 5/2002 | Yamazaki et al. | 536/4.1 |
| 6,444,795 B1 | * | 9/2002 | Yamazaki et al. | 536/4.1 |
| 6,518,248 B1 | * | 2/2003 | Yamazaki et al. | 514/25 |
| 6,518,410 B2 | * | 2/2003 | Yamazaki et al. | 536/4.1 |
| 2002/0028776 A1 | | 3/2002 | Yamazaki et al. | |
| 2002/0052327 A1 | * | 5/2002 | Yamazaki et al. | 514/25 |
| 2002/0173471 A1 | * | 11/2002 | Yamazaki et al. | 514/24 |

FOREIGN PATENT DOCUMENTS

| | | | |
|---|---|---|---|
| JP | 55130996 | * | 10/1980 |
| JP | 03052815 | * | 3/1991 |
| JP | 03052816 | * | 3/1991 |
| JP | 03066603 | * | 3/1991 |
| JP | 60040159 | * | 9/1991 |
| JP | 03246203 | * | 11/1991 |
| JP | 7-149786 | | 6/1995 |
| JP | 7-242691 | | 9/1995 |
| JP | 11106395 | * | 4/1999 |
| JP | 2000-143516 | | 5/2000 |
| WO | WO 91/02521 | | 3/1991 |
| WO | WO 97/40838 | | 11/1997 |
| WO | WO 00/53190 | | 9/2000 |

OTHER PUBLICATIONS

Peer et al., "Synthesis of an L–Fucose–Derived Cyclic Nitrone and its Conversion to α–L–Fucosidase Inhibitors," *Helvetica Chemica Acta*, 82(7), 1044–1065 (Jul. 7, 1999).††*

Sanders et al., "Synthesis of Sulfated Trisaccharide Ligands for the Selectins," *Tetrahedron*, 53(48), 16391–16422 (Dec. 1, 1997).††*

Arasappan et al., "Regiospecific 4, 6–Functionalization of Pyranosides via Dimethylboron Bromide–Mediated Cleavage of Phthalide Orthoesters," *J.American Chemical Society*, 117(1), 177–183 (Jan. 11, 1995).††*

Thiem et al., "Synthesen von Methyl1–4–O–(β–D–curaocsyl)–α–D–curamicosid, dem Glycosid der Disaccharideinheit E–F von Flamabamycin und Isomeren," *Justus Liebig's Annalen der Chemie*, 1987(4), 289–295 (Apr., 1987).††*

Fujimaki et al., "Conversion of 1, 6–Anhydromaltose into Pseudodisaccharides Containing Aminocyclitols as Constituent," *Agricultural & Biological Chemistry*, 44(9), 2055–2059 (Sep., 1980).††*

Tulloch et al., "Combination and Positional Distribution of Fatty Acids in Plant Sulfolipids," *Hoppe–Seyler's Zeitschrift Physiol. Chem.*, 354, 879–889 (Aug., 1973).††*

Fusetani et al., "Structures of Two Water Soluble Hemolysins Isolated from the Green *Ulva pertusa*," *Agricultural and Biological Chemistry*, 39(10), 2021–2025 (Oct., 1975).††*

Kitagawa et al., "Sulfoglycolipid from the Sea Urchin *Anthocidaris vrassisspina* A. Agassiz," *Chemical & Pharmaceutical Bulletin*, 27(8), 1934–1937 (Aug., 1979).††*

(List continued on next page.)

Primary Examiner—James O. Wilson
Assistant Examiner—L E Crane
(74) Attorney, Agent, or Firm—Frishauf, Holtz, Goodman & Chick, P.C.

(57) ABSTRACT

Sulfofucosylacylglycerol derivatives represented by General Formula (1):

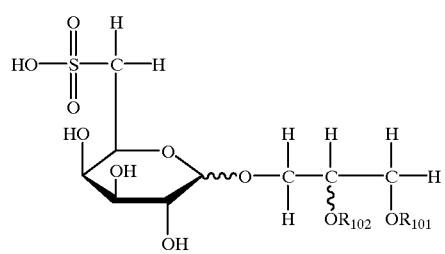

(1)

where $R_{101}$ represents an acyl residue of a higher fatty acid and $R_{102}$ represents a hydrogen atom or an acyl residue of a higher fatty acid. The derivatives represented by General formula (1) are useful as a DNA polymerase inhibitor and an anticancer agent.

24 Claims, No Drawings

OTHER PUBLICATIONS

Gustafson et al., "AIDS–Antiviral Sulfolipids From Cyanobacteria (Blue–Green Algae)," *Journal of the National Cancer Institute(USA)*, 81(16), 1255–1258 (Aug. 16, 1989).††*

Adebodun et al., "Spectroscopic Studies of Lipids and Biological Membranes: Carbon–13 and Proton Magic–Angle Sample–Spinning Nuclear Magnetic Resonance Study of Glycolipid–Water Systems," *Biochemistry*, 31(18), 4502–4509 (May, 1992).††*

Gage et al., "Comparison of Sulfoquinovosyl Diacylglycerol from Spinach and the Purple Bacterium *Rhodobacter sphaeroides* by Fast Atom Bombardment Tandem Mass Spectrometry," *Lipids*, 27(8), 632–636 (Aug., 1992).††*

Morimoto et al., "Studies on Glycolipids. VII. Isolation of Two New Sulfoquinovosyl Diacylglycerols from the Green Alga *Chlorella vulgaris*," *Chemical & Pharmaceutical Bulletin*, 41(9), 1545–1548 (Sep., 1993).††*

Amarquaye et al., "A New Glycolipid from *Byrsonima crassifolia*," *Planta Medica*, 60(1), 85–86 (Feb., 1994).††*

Murakami et al., "Enzymatic Transformation of Glyceroglycolipids into sn–1 and sn–2 Lysoglyceroglycolipids by Use of *Rhizopus arrhizus* Lipase," *Tetrahedron*, 50(7), 1993–2002 (Feb. 14, 1994).††*

Vishwanath et al., "Interaction of Plant Lipids with 14 kDa Phospholipase $A_2$ Enzymes," *Biochemical Journal*, 320(1), 93–99 (Nov. 15, 1996).††*

Golik et al., "Isolation and Structure Determination of Sulfonoquinovosyl Dipalmitoyl Glyceride, a P–Selectin Receptor Inhibitor from the Alga *Dictyochloris Fragrans*," *Journal of Natural Products*, 60(4), 387–389 (Apr., 1997).††*

Vasänge et al., "A Sulfonoglycolipids from the Fern *Polypodium decumanum* and its Effect on the Platelet Activating–factor Receptor in Human Neutrophils," *Journal of Pharmaceutical Pharmacology*, 49(5), 562–566 (May, 1997).††*

Kim et al., "Structural Identification of Glycerolipid Molecular Species Isolated from Gyanobacterium Synechocytis sp. PCC 6803 Using Fast Atom Bombardment Tandem Mass Spectrometry," *Analytical Biochemistry*, 267, 260–270 (1999).††*

S. Kashima et al., "A Study of Polymerase Inhibitors of Higher Plants", Nippon Nogeikagaku Kaishi, vol. 72, Mar. 5, 1998, p. 82.

K. Ohta et al, Action of a New Mammalian DNA Polymerase Inhibitor, Sulfoquinosyldiacylglycerol, *Biological & Pharmaceutical Bulletin*, Feb. 1999, vol. 22, No. 2, pp. 111–116.

K. Ohta et al., Sulfoquinovosyldiacylglycerol, KM043, a New Potent Inhibitor of Eukarytic DNA Polymerase and HIV–Reverse Transcriptase Type 1 from a Marine Red Alga, *Gigartina tenella, Chemical & Pharmaceutical Bulletin*, 1998, vol. 46, No. 4, pp. 684–686. (Apr., 1998).

Y. Mizushima et al., "Studies on Inhibitors of Mammalian DNA Polymerase alpha and beta", *Biochemical Pharmacology*, 1998, vol. 55, No. 4, pp. 537–541.

H. Sahara et al., "In vivo anti–tumor effect of 3'–sulfonoquinovosyl 1'–monoacyl–glyceride isolated from sea urchin (*Stronglocentrotus intermedius*) intestine", *British Journal of Cancer*, 1997, vol. 75, No. 3, pp. 324–332.

P.Q. Liem et al., "Structures teneurs et compositions des esters sulfuriques sulfoniques, phosphoriques des glycosyl-diglycerides de trois fucacees", *Biochimie*, 1976, vol. 58, pp. 1367–1380.

Yoshiyuki Mizushina, Shonen Yoshida, Akio matsukage and Kengo Sakaguchi, "The Inhibiting Action of Fatty Acids on DNA Polymerase β", *Biochimica et Biophysica Acta*, 1336, (1997), 509–521.

Dana M. Gordon et al., "Synthesis of a Cyanobacterail Sulfolipid: Confirmation if Its Structure, Stereochemistry, and Anti–HIV–1 Activity", *J. Amer. Chem. Soc.*, 114, 659–663 (1992).

Roy Gigg et al., "Synthesis of 3–O–(6–Deoxy–6–sulpho–α–D–glucopyranosyl)–1, 2–di–O–hexadecanoyl–L–glycerol, 'Sulphoquinovosyl Diglyceride'", *Journal of the Chemical Society Perkin Transaction I* 2490–2493 (1980).

Michael Keusgen et al., "Sulfoquinovosyl Diacylglycerols from the Alga *Heterosigma carterae*", *Lipids*, 1101–1112, 32, (1997). (Oct., 1997).

Byeng Wha Son, "Glycolipids from Byrsonima Crassifolia", *Phytochemistry*, 45, 647–650 (1997).

Shirahashi et al., "Isolation and Identification of Anti–Tumor–Promoting Principles From the Fresh–Water Cyanobacterium *Phormidium tenue*", *Chem. Pharm. Bull.*, 41, (9), 1664–1666 (1993).

Mizushina et al., "Search and Structural Identification of Inhibitory Substance on DNA Polymerase of Higher Organisms," published in *A Collection of Summaries of Lectures at Convention of Natural Organic Compounds*, published by Prof. K. Sakai (Kyushu University) and the Organizing Committee of the 40th Symposium on the Chemistry of Natural Products, Fukuoka, Japan, Aug. 31, 1998, only pp. 493–498 supplied.*

H Nakane & K Ono, "Inhibitor of DNA Polymerase Activity," *Metabolism*, 28(12), 1027–1034 (1991).*

Ogawa et al., "Sulfated Glycoglycerolipid from Archaebacterium Inhibits Eukaryotic DNA Polymerase α, β and Retroviral Reverse Transcriptase and Affects Methyl Methanesulfonate Toxicity," *International Journal of Cancer*, 76, 512–518 (1998).*

Kretzschmar et al., "Short Synthesis of Sulfatide–and SQDG–Mimetics as Small Molecular Weight Selectin Inhibitors," *Tetrahedron*, 54, 15189–15198 (1998).*

Meyer et al., "Synthesis of Benzyl 6–O–Sulfo–β–D–Glycopyranoside Salts and Their 6–β–Deuterated Analogues. Conformational Preferences of Their (Sulfonyloxy)methyl Group," *Journal of Organic Chemistry*, 55, 902–906 (1990).*

* cited by examiner

SULFOFUCOSYLACYLGLYCEROL DERIVATIVES AND ADMINISTRATION THEREOF AS MEDICAMENTS

CROSS-REFERENCE TO RELATED APPLICATIONS

This is a Continuation-in-Part Application of PCT Application No. PCT/JP00/00974, filed Feb. 21, 2000, which was not published under PCT Article 21(2) in English.

This application is based upon and claims the benefit of priority from the prior Japanese Patent Application No. 11-051398, filed Feb. 26, 1999, the entire contents of which are incorporated herein by reference.

BACKGROUND OF THE INVENTION

1. Field of the Invention

The present invention relates to novel sulfofucosylacylglycerol derivatives. The novel sulfofucosylacylglycerol derivatives of the present invention are useful as medicaments, more specifically, a DNA polymerase inhibitor and an anticancer agent.

2. Description of the Related Art

Sulfur-containing glycolipids contained in natural products derived from, e.g., algae and higher plants are known to have physiological activities.

For example, in a document of Ohta et al. (Chemical & Pharmaceutical Bulletin, 46(4), (1998)), it is described that a specific sulfoquinovosyldiacylglycerol derivative derived from red algae, Gigartina tenella, exhibits not only inhibitory activities against DNA polymerases α and β of higher organisms but also an inhibitory activity against HIV-derived reverse-transcriptase.

Furthermore, in a document of Mizushina et al. (Biochemical Pharmacology 55, 537–541 (1998)), it is described that specific sulfoquinovosyldiacylglycerol derivatives derived from a pteridophyte exhibits inhibitory activities against a calf DNA polymerase a and a rat DNA polymerase β, but does not have any influence on the inhibitory activity against HIV-derived reverse-transcriptase.

On the other hand, in a document of Sahara et al. (British Journal of Cancer, 75(3), 324–332 (1997)), it is described that a fraction of sulfoquinovosylmonoacylglycerols obtained from sea urchin intestine exhibits anticancer activities in-vivo and in-vitro.

However, sulfur-containing glycolipids disclosed in Ohta et al., Mizushina et al., and Sahara et al., are sulfoquinovosylacylglycerol derivatives having an α-quinovose (i.e., 6-deoxy-α-glucose) as a sugar component thereof. A sulfur-containing glycolipids having a fucose (i.e., 6-deoxygalactose) as a sugar component has not yet been known.

Furthermore, National Patent Publication No. 5-501105 describes that a sulfoquinovosyldiacylglycerol derivative has an anti-virus activity. More specifically, it discloses that the derivative has an anti-HIV (human immunodeficiency virus) activity, however it does not disclose that the derivative has inhibitory activities against DNA polymerase and anticancer activities.

BRIEF SUMMARY OF THE INVENTION

An object of the present invention is to provide a novel sulfofucosylacylglycerol derivative having a fucose as a sugar component and its use as a medicament.

The present invention provides compounds represented by the following General Formula (1):

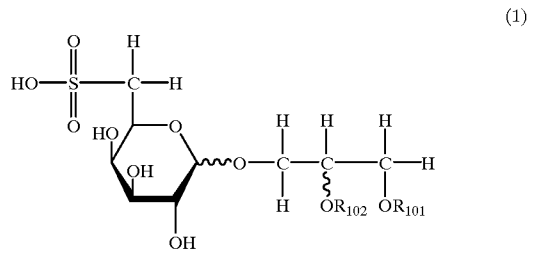

wherein $R_{101}$ represents an acyl residue of a higher fatty acid, and $R_{102}$ represents a hydrogen atom or an acyl residue of a higher fatty acid.

Furthermore, the present invention also provides medicaments containing, as an active ingredient, at least one compound selected from the group consisting of the compounds represented by General Formula (1) and pharmaceutically acceptable salts thereof.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

DETAILED DESCRIPTION OF THE INVENTION

In the specification, the term "carbon atoms" of a protecting group refers to the number of carbon atoms assuming that the protecting group is unsubstituted. To be more specific, when the group represented by $R^1$ is a substituted alkyl group, its number of carbon atoms is that of the alkyl group itself, and the number of carbon atoms of the substituent on the alkyl group is not counted. The same conditions are applicable to the case where the protecting group is other than the alkyl group.

First, the sulfofucosylacylglycerol derivative (hereinafter, also referred to as "sulfofucosylacylglycerol derivative of the present invention") represented by General Formula (1) of the present invention will be more specifically explained.

The sulfofucosylacylglycerol derivative of the present invention is represented by following General Formula (1):

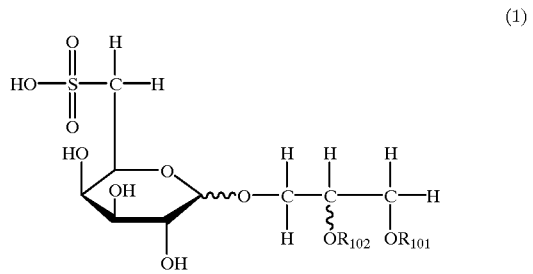

wherein $R_{101}$ represents an acyl residue of a higher fatty acid, and $R_{102}$ represents a hydrogen atom or an acyl residue of a higher fatty acid.

In General Formula (1), RIO represents an acyl residue of a higher fatty acid. The fatty acids providing the acyl residues represented by $R_{101}$ includes straight-chain or branched-chain, saturated or unsaturated higher fatty acids.

When the sulfofucosylacylglycerol derivative of the present invention is used as a medicament, $R_{101}$ is preferably an acyl residue of a straight-chain saturated higher fatty acid in view of its anticancer activity, in particular, against a solid tumor, for example, gastric cancer and colon cancer, and more preferably a group represented by $CH_3(CH_2)_nCO-$ (wherein n is an integer of 12–24, preferably an even number of 12–24). The present inventors predict that sulfofucosylacylglycerol derivatives, where $R_{101}$ of General Formula (1) of the invention is represented by $CH_3(CH_2)_nCO-$ (n>24), may also have an anticancer activity. However, the sulfofucosylacylglycerol derivatives having such long-chain acyl residues are not used in practice in view of manufacturing cost and the like.

In General Formula (1) mentioned above, $R_{102}$ represents a hydrogen atom or an acyl residue of a higher fatty acid. The fatty acids providing the acyl residues include straight-chain or branched-chain, saturated or unsaturated higher fatty acids, and more specifically, include the same fatty acids as those mentioned above for $R_{101}$.

When the sulfofucosylacylglycerol derivatives of the present invention are used as a medicament, $R_{102}$ is preferably a hydrogen atom in view of their anticancer activities, in particular, against solid tumor, for example, gastric cancer and colon cancer.

In General formula (1), the sugar skeleton of the sulfofucoside may be either a boat or chair configuration. However, the chair configuration is preferable in view of stability. Furthermore, the bonding between sulfofucose and glycerol is either an α- or β-bonding. Furthermore, the absolute configuration of the carbon (asymmetric carbon) at the 2-position of the glycerol moiety may be either the S- or R-configuration.

Now, a method of preparing the sulfofucosylacylglycerol derivatives of the present invention will be explained below.

The sulfofucosylacylglycerol derivatives of the present invention can be prepared via (Step A) to (Step J) in accordance with the reaction procedure shown in Scheme 1 below:

Scheme 1

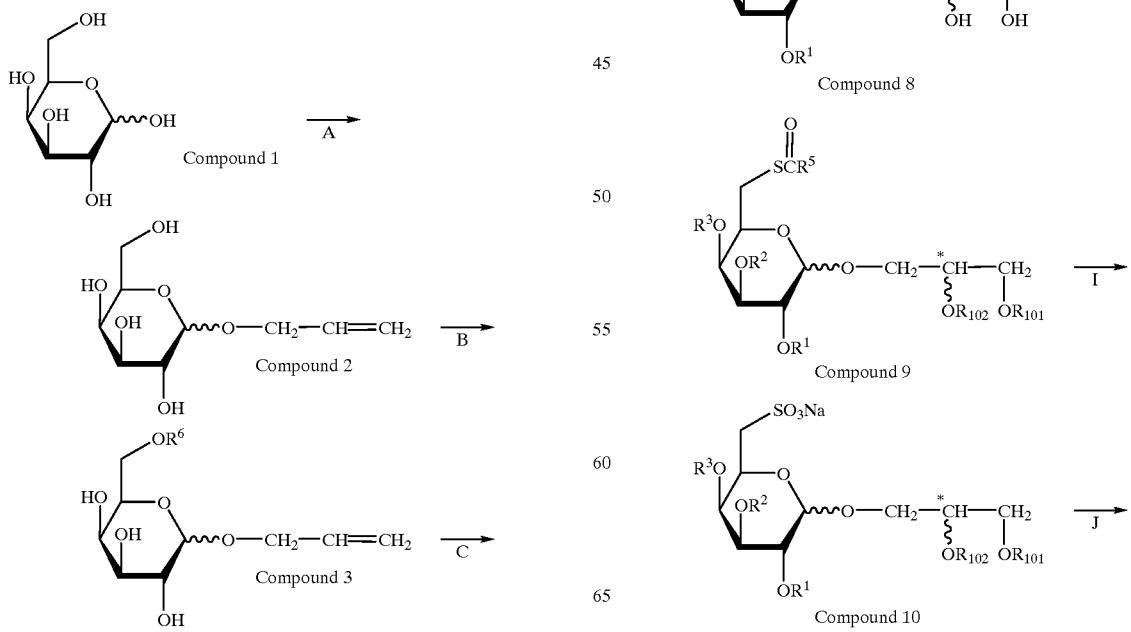

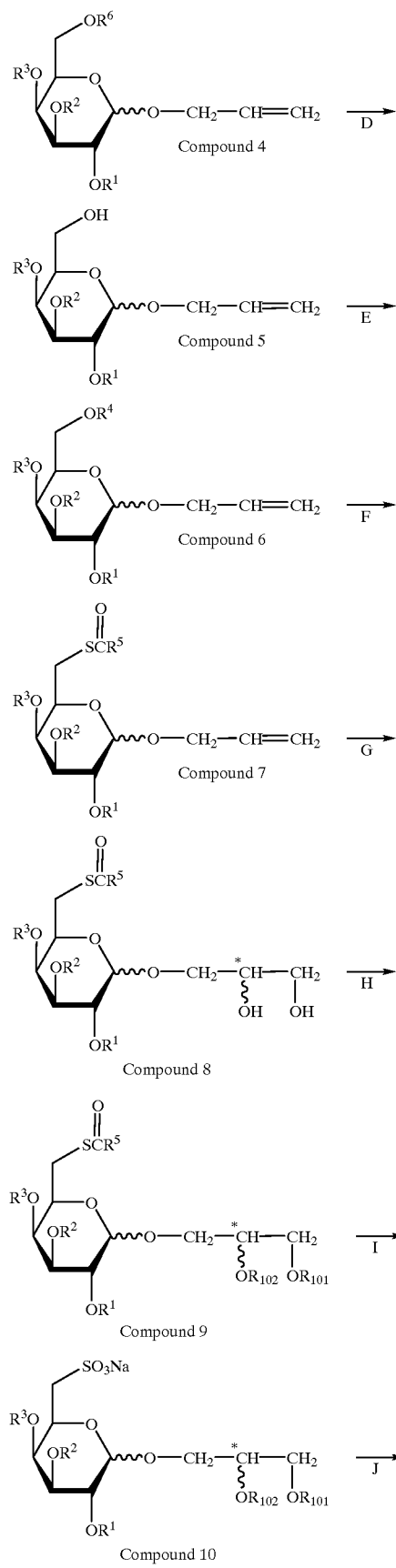

-continued

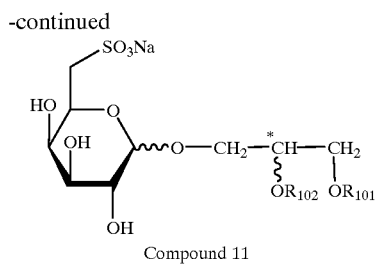

Compound 11

(Step A) The hydroxyl group bonded to the C1 carbon of the D-galactose is converted into a 2-propenyl group. (Step B) The hydroxyl group of the C6 carbon of the galactose is protected. (Step C) The hydroxyl groups bonded to the C2, C3 and C4 carbons of the galactose are protected. (Step D) The protecting group of the C6 carbon previously protected is deprotected. (Step E) The hydroxyl group bonded to the C6 carbon is substituted with a group (for example, an alkylsulfonyloxy group or arylsulfonyloxy group) which can be converted to a carbonylthio group. (Step F) The C6 carbon is converted into a carbonylthio group. (Step G) The 2-propenyl group bonded to the C1 carbon is converted into a diol. (Step H) Both of the hydroxyl groups or only the hydroxyl group at the 1-position of the diol thus obtained are/is esterified with a desired higher fatty acid. (Step I) The carbonylthio group at the C6 carbon is converted into a sulfonate salt. (Step J) The protecting groups of C2, C3 and C4 carbons of the sulfonate salt obtained are deprotected. As a result, a salt of a sulfofucosylacylglycerol derivative of the present invention can be produced. The salt thus obtained is subjected to titration with an acid such as hydrochloric acid to give the sulfofucosylacylglycerol derivative of the present invention.

The aforementioned Steps A–J will be further explained in detail.

In Step A, the 2-propenylation is carried out by reacting the galactose with allyl alcohol in the presence of a strong acid, such as trifluoromethanesulfonic acid, usually at room temperature to 100° C., preferably from 80 to 90° C., for a half day to two days. However, the reaction time varies depending upon the reaction conditions.

In Step B, the hydroxyl group bonded to the C6 carbon is protected to obtain the compound to which -$OR^6$ is bonded at the C6 carbon (where $R^6$ represents an alkyl or substituted silyl group).

As the compound capable of protecting the hydroxyl group, a compound can be used which can provide an alkyl group or substituted silyl group as the $R^6$ group.

Examples of the alkyl group represented by $R^6$ preferably include bulky and substituted alkyl groups. The substituents of the bulky and substituted alkyl groups include methyl and phenyl groups. The specific examples of the substituted alkyl group include t-butyl and trityl groups.

When the group represented by $R^6$ represents a substituted silyl group, examples of substituents of the substituted silyl group include lower alkyl groups, preferably alkyl groups having 1–4 carbon atoms (for example, methyl, ethyl, isopropyl and t-butyl groups); and aryl groups, preferably aryl groups having 6 carbon atoms (for example, a phenyl group). The substituted silyl group represented by $R^6$ preferably includes tri-substituted silyl groups, more preferably, a t-butyldiphenylsilyl group.

When the compound 3, where $R^6$ represents an alkyl group, is to be obtained, the protection of the hydroxyl group in Step B can be carried out by adding a compound represented by $R^6$-X (where $R^6$ represents the alkyl group defined above, and X represents a halogen atom such as chlorine atom) to a solution of the compound 2 dissolved in an organic solvent, such as anhydrous pyridine, and reacting the solution mixture at room temperature in the presence of a catalyst such as p-dimethylaminopyridine (DMAP). As the compound $R^6$-X, trityl chloride is preferably used in view of manufacturability and reactivity.

When the compound 3, where $R^6$ represents a substituted silyl group, is to be obtained, t-butyldiphenylsilyl chloride, for example, is used as the compound $R^6$-X, and the reaction is carried out usually in the presence of a catalyst, such as imidazole, at room temperature for a half day to two days. Note that the reaction time varies depending upon the reaction conditions.

In Step C, the hydroxyl groups bonded to the C2, C3 and C4 carbons are protected and converted into —$OR^1$, —$OR^2$ and —$OR^3$, respectively, where $R^1$ to $R^3$ independently represent an alkyl or substituted silyl group. The protection of these hydroxyl groups can be carried out by activating, with sodium hydride, the hydroxyl groups bonded to the C2, C3 and C4 carbons of the compound 3 dissolved in an organic solvent, such as N,N-dimethylformamide (DMF), and reacting with the compound capable of protecting these hydroxyl groups at room temperature.

As the compound capable of protecting the hydroxyl groups, benzyl bromide, p-methoxybenzyl bromide, t-butyldimethylsilyl chloride or triethylsilyl chloride may be used. Benzyl bromide is preferably used as the protecting group in view of stability of the protecting group in the case where the acyl residue(s) represented by $R_{101}$ and/or $R_{102}$ are/is saturated one(s). The reaction using the compound capable of protecting the hydroxyl groups can be carried out under a suitable reaction condition for each of the protecting groups.

The deprotection of the protecting group bonded to the C6 carbon in Step D may be carried out by reacting a solution of the compound 4 dissolved in an organic solvent, such as methanol, in the presence of a catalyst, such as p-toluenesulfonic acid, generally for 12 hours to one day at room temperature. The reaction time varies depending upon the reaction conditions.

In Step E, $R^4$, that is, an alkylsulfonyl or arylsulfonyl group is bonded to the hydroxyl group at the C6 carbon of the compound 5, so that the hydroxyl group is converted into —$OR^4$ to give the compound 6.

The reaction to give the —$OR^4$ group is performed by adding a compound having the alkylsulfonyl group or a compound having the arylsulfonyl group to a solution of the compound 5 dissolved in an organic solvent, and reacting them. The alkyl group of the compound having the alkylsulfonyl group preferably includes unsubstituted alkyl groups, more preferably, lower alkyl groups, much more preferably, alkyl groups having 1–2 carbon atoms (methyl and ethyl groups). The compound having an alkylsulfonyl group can be represented by $R^{4'}$-x (where $R^{4'}$ represents an alkylsulfonyl group, and X represents a halogen atom). Specific examples include methanesulfonyl chloride and ethanesulfonyl chloride.

On the other hand, the aryl group of the compound having the arylsulfonyl group may include unsubstituted and substituted aryl groups, preferably aryl groups having 6 carbon atoms (e.g., a phenyl group). In the case of the substituted aryl group, examples of the substituent thereof include p-methyl and p-methoxy groups. Examples of the compound having an arylsulfonyl group include compounds represented by $R^{4''}$-X (where $R^{4''}$ represents an arylsulfonyl group, and X represents a halogen atom). Specific examples include p-toluenesulfonyl chloride, p-methoxybenzenesulfonyl chloride and benzenesulfonyl chloride.

Of the compounds having an alkylsulfonyl or arylsulfonyl group, a compound having a p-toluenesulfonyl group (tosyl group) is preferably used from the viewpoint of reaction facility.

In the reaction of Step E, as an organic solvent, for example, pyridine or dichloromethane may be used.

The reaction mentioned above may be performed, as the case may be, in the presence of a catalyst, such as DMAP, at room temperature for 2 hours to one day. The reaction time varies depending upon the reaction conditions.

In Step F, the sulfonyloxy group ($-OR^4$) of the compound 6 is replaced with a carbonylthio group represented by $-SC(=O)R^5$, where $R^5$ represents a hydrogen atom, an alkyl or aryl group.

In the reaction, a compound capable of substituting the alkylsulfonyloxy or arylsulfonyloxy group of the compound 6 with the carbonylthio group, is allowed to react in an organic solvent to give a compound 7. Hereinafter, this compound will be referred to as "O-substituted→S-substituted compound".

Examples of the O-substituted→S-substituted compound include alkali metal salts and alkali earth metal salts of a thiocarboxylic acid. Examples of the thiocarboxylic acid include thioformic acid, lower thiocarboxylic acids, preferably aliphatic thiocarboxylic acids each having 1–2 carbon atoms in its aliphatic hydrocarbon moiety (for example, thioacetic acid or thiopropionic acid), and aromatic thiocarboxylic acids each having 6–10 carbon atoms in its aromatic hydrocarbon moiety (for example, thiobenzoic acid).

The alkali metal that forms a salt with the thiocarboxylic acid includes potassium and sodium. The alkali earth metal includes magnesium and calcium.

Of the above-mentioned O-substituted→S-substituted compounds, salts of thioacetic acid may be preferably used since a reaction can proceed stably and the sulfur atom can be easily oxidized in a later step.

Examples of an organic solvent used in the reaction include hexamethylphosphoramide, N,N-dimethylformamide and dimethylsulfoxide.

The aforementioned reaction may be performed usually at room temperature to around 100° C. while stirring for one hour to one day. Note that the reaction time varies depending upon the reaction conditions.

The dihydroxylation of Step G may be performed by adding an oxidizing agent, such as osmium tetraoxide, to a solution of the compound 7 dissolved in a solvent mixture, such as a mixture of t-butanol and water, and then reacting the resultant mixture in the presence of a re-oxidizing agent, such as trimethylamine N-oxide, at room temperature for one hour to one day. Note that the reaction time varies depending upon the reaction conditions.

By the esterification of Step H, a sulfofucosylacylglycerol derivative having a desired higher fatty acid bonded, through an ester-bond, to its glycerol moiety can be obtained. This reaction can be carried out by adding a fatty acid corresponding to a final product to a solution of the compound 8 dissolved in a suitable organic solvent, such as dichloromethane, and then reacting the resultant mixture, if necessary, in the presence of a suitable catalyst, such as ethyldimethylaminopropylcarbodiimide (EDCI)-DMAP.

In the reaction of Step H, as the fatty acid to be added, use may be made of a higher fatty acid whose acyl group is that represented by $R_{101}$ of General Formula (1).

In the reaction of Step H, the compound 9 is obtained in the form of a mixture of a diacylester and a monoacylester. The diacylester herein is represented by Formula (1) of the present invention where each of $R_{101}$ and $R_{102}$ is an acyl residue of the higher fatty acid added. The monoacylester herein has the acyl residue of the higher fatty acid added, as the $R_{101}$ only. Two or more higher fatty acids may be added, if desired, in the reaction of Step H. In this case, the resultant mixture contains diacylesters represented by General Formula (1) where $R_{101}$ and $R_{102}$ are the same or different acyl residues, and monoesters having different acyl residues as $R_{101}$.

If necessary, the mixture of the monoesters and diesters can be isolated from each other by, for example, chromatography, and subjected to the next reaction Step I.

Furthermore, if desired, by reacting a monoester obtained in Step H with a fatty acid having a different acyl residue from the acyl residue ($R_{101}$) of the monoester, it is possible to obtain a diester where $R_{102}$ and $R_{101}$ are different acyl residues. This additional esterification step may be performed under the same conditions as those of Step H except that a different fatty acid is used.

In Step I, the conversion into a sulfonate salt can be carried out by adding an oxidizing agent, for example, OXONE ($2KHSO_5$, $KHSO_4$ and $K_2SO_4$) into a solution of the compound 9 dissolved in an organic solvent, which is buffered with acetic acid and potassium acetate, and then allowing the resultant mixture to react at room temperature for 12–24 hours. Note that the reaction time varies depending upon the reaction conditions.

The deprotection of the protecting groups bonded to carbons at the C2 to C4 carbons in Step J can be carried out by a method suitable for a protecting group to be used and an acyl residue of the bonded higher fatty acid. For example, when the protecting group is a benzyl group and each of $R_{101}$ and $R_{102}$ is an acyl residue of a saturated higher fatty acid, the deprotection can be conducted by reacting a solution of a compound 10 dissolved in an organic solvent, such as ethanol, in the presence of a catalyst, such as palladium-activated carbon, under a hydrogen gas atmosphere at room temperature. Furthermore, when at least one of the acyl residues of the higher fatty acids represented by $R_{101}$ and $R_{102}$ is an acyl residue of an unsaturated higher fatty acid, a deprotection method suitable for a protecting group used and capable of retaining the double bond of the unsaturated fatty acid may be employed. For example, when the protecting group is a silyl group, the deprotection can be conducted by use of an acid catalyst (e.g., trifluoroacetic acid).

Note that the galactose of a starting material usually takes α- and β-anomer configurations in a solution. Therefore, the product in each step results in a mixture of α- and β-anomers. The mixture may be separated into α- and β-anomers by chromatography. Furthermore, α-anomer may be separated by carrying out crystallization after Step A.

Now, we will explain the medicaments of the present invention containing at least one compound selected from the group consisting of sulfofucosylacylglycerol derivatives of the present invention and pharmaceutically acceptable salts thereof, as an active ingredient.

The sulfofucosylacylglycerol derivative serving as an active ingredient for the medicaments of the present invention may be an isomer in which the fucosyl moiety is bonded to glyceridyl moiety with an α- or β-configuration. The derivative may be an isomer regarding the asymmetric carbon at the C2 carbon of the glyceridyl moiety. The medicaments of the present invention may include one of these isomers alone or in combination of two or more isomers as long as they do not adversely affect the activity.

In the present invention, the medicinal use includes a DNA polymerase inhibitor and an anticancer agent.

Examples of the pharmaceutically acceptable salts employed in the medicament of the present invention include, but not limited to, a salt of a monovalent cation such as a sodium or potassium ion.

Hereinafter, the compounds of the group consisting of sulfofucosylacylglycerol derivatives and pharmaceutically acceptable salts thereof are sometimes referred to as "medicinally active substance of the present invention".

The medicinally active substance of the present invention can be orally or parenterally administered. Medicinally active substance of the present invention can be combined with, for example, a pharmaceutically acceptable excipient or diluent depending on an administration route thereby to form a medicinal formulation.

The forms of the agent suitable for oral administration include, solid-, semi-solid, liquid- and gas-states. Specific examples include, but not limited to, tablet, capsule, powder, granule, solution, suspension, syrup and elixir agents.

In order to formulate the medicinally active substance of the present invention into tablets, capsules, powders, granules, solutions or suspensions, the substance is mixed with a binder, a disintegrating agent and/or a lubricant, and, if necessary, the resultant is mixed with a diluent, a buffer, a wetting agent, a preservative and/or a flavor, by a known method. Examples of the binder include crystalline cellulose, cellulose derivatives, cornstarch and gelatin. Examples of the disintegrating agent include cornstarch, potato starch and sodium carboxymethylcellulose. Examples of the lubricant include talc and magnesium stearate. Furthermore, additives such as lactose and mannitol may also be used as long as they are used conventionally.

Moreover, the medicinally active substance of the present invention may be administered in the form of aerosol or inhalant, which is prepared by charging the active substance of liquid- or fine powder-form, together with a gaseous or liquid spraying agent, and, if necessary, a known auxiliary agent such as a wetting agent, into a non-pressurized container such as an aerosol container or a nebulizer. As the spraying agent, a pressurized gas, for example, dichlorofluoromethane, propane or nitrogen may be used.

For parenteral administration, the medicinally active agent of the present invention can be injected by, for example, rectal administration or injection.

For rectal administration, a suppository may be used. The suppository may be prepared by mixing the medicinally active substance of the present invention with an excipient that can be melted at body temperature but is solid at room temperature, such as cacao butter, carbon wax or polyethylene glycol, and molding the resultant material, by a known method.

For the administration by injection, the medicinally active agent of the present invention can be injected hypodermically, intracutaneously, intravenously or intramuscularly. An injection preparation may be formulated by dissolving, suspending or emulsifying the medicinally active substance of the invention into an aqueous or non-aqueous solvent such as a vegetable oil, a synthetic glyceride with a fatty acid, an ester of a higher fatty acid or propylene glycol by a known method. If desired, a conventional additive such as a solubilizing agent, an osmoregulating agent, an emulsifier, a stabilizer or a preservative, may be added to the preparation.

For formulating the medicinally active substance of the invention into solutions, suspensions, syrups or elixirs, a pharmaceutically acceptable solvent such as sterilized water for injection or normalized physiological saline solution may be used.

The medicinally active substance of the invention may be used together with a pharmaceutically acceptable compound having another activity, to prepare a medicinal preparation.

The dose of the medicinally active substance of the present invention may be appropriately set or adjusted in accordance with an administration form, an administration route, a degree or stage of a target disease, and the like. For example, in the case of oral administration, a dose of the medicinally active substance may be set at 1–10 mg/kg body weight/day. In the case of administration by injection, a dose of the medicinally active substance may be set at 1–5 mg/kg body weight/day. In the case of rectal administration, a dose of the medicinally active substance may be set at 1–5 mg/kg body weight/day. However, the dose is not limited to these.

When the medicinally active substance of the present invention is used as an anticancer agent, examples of cancers to be treated include those having features of malignant tumors such as solid tumors including adenocarcinoma, epithelioma, sarcoma, glioma, melanoma and lymphoma, and a fluid cancer such as leukemia.

EXAMPLES

The present invention will now be described by way of its Examples. However, the present invention is not limited to these Examples.

SYNTHESIS EXAMPLE

A preparation procedure of a sulfofucosylacylglycerol derivative will be shown in Scheme 2 by way of a a-sulfofucosylacylglycerol.

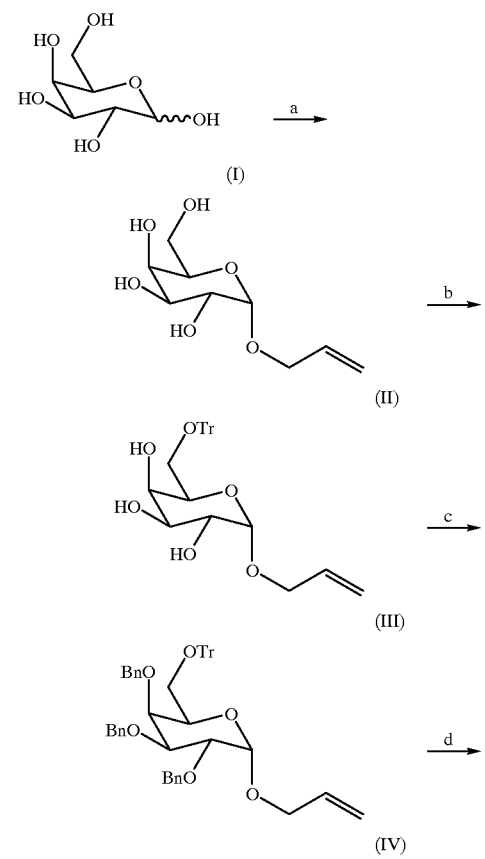

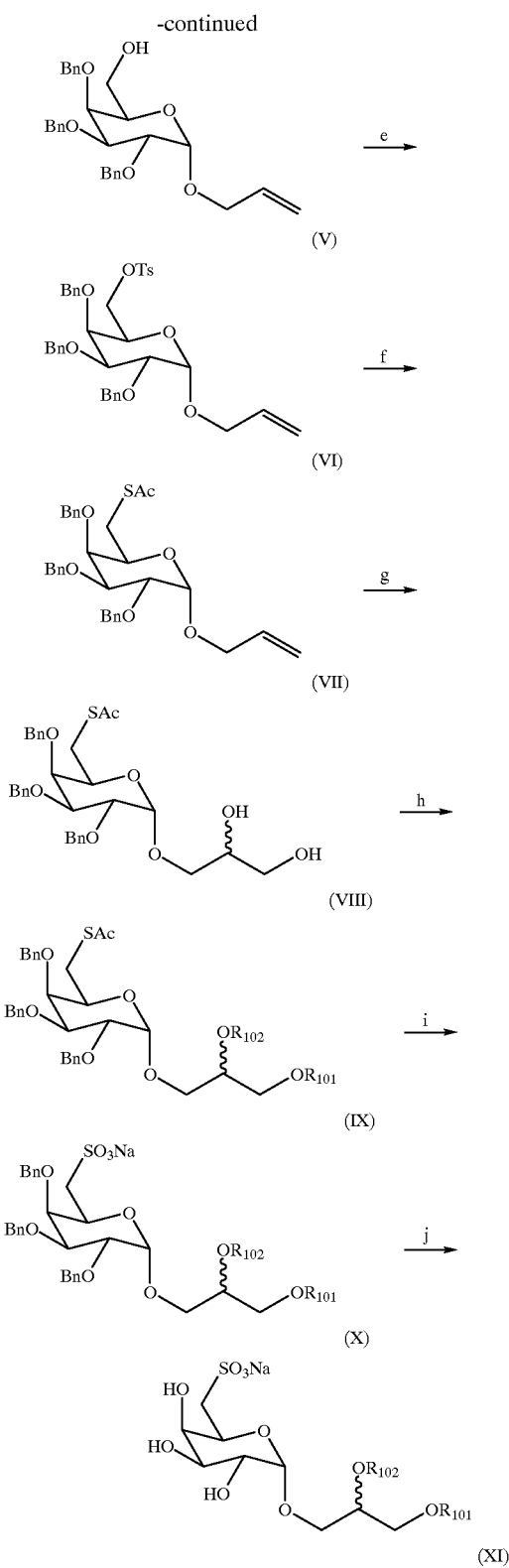

Tr=trityl group, Bn=benzyl group, Ts=tosyl group, AcS= acetylthio group,
$R_{101}$=an acyl residue of a higher fatty acid, and
$R_{102}$=a hydrogen atom or an acyl residue of a higher fatty acid Reaction conditions:
a; allyl alcohol, trifluoromethanesulfonic acid, at 90° C.
b; pyridine, tritylchloride, p-dimethylaminopyridine (DMAP), at room temperature
c; sodium hydride, benzylbromide, N,N-dimethylformamide, at room temperature
d; methanol, p-toluenesulfonic acid monohydrate at room temperature
e; pyridine, p-toluenesulfonyl chloride, DMAP, at room temperature
f; ethanol, potassium thioacetate, under reflux
g; t-butanol, water, osmium tetraoxide, trimethylamine N-oxide dihydrate, at room temperature
h; dichloromethane, fatty acid, DMAP 1-ethyl-3-(3-dimethylaminopropyl)-carbodiimide hydrochloride, at room temperature
i; acetic acid, potassium acetate, OXONE, at room temperature
j; ethanol, palladium-activated carbon, hydrogen, at room temperature In Scheme 2, a mixture of a monoester and diester obtained in Step h is separated by chromatography and each ester may be subjected to Step i.

Example 1

Route a: 1-O-(2-propenyl)-α-D-galactose (II)

Into 140 mL of allyl alcohol, 50.0 grams (278 mmol) of D-galactose (I) was added and sufficiently dissolved therein. To the solution, 0.5 mL of trifluoromethanesulfonic acid was gradually added under an ice-cooled condition. Then, the solution was reacted in an oil bath at 80° C. for 24 hours while stirring. At the stage where the reaction sufficiently proceeded, the reaction mixture was neutralized with 1.0 mL of triethylamine, concentrated in vacuo, and purified by silica gel flash chromatography (chloroform: methanol= 6:1→5:1→4:1), to give a pale yellowish oily substance. The product was dissolved in hot ethanol and cooled to crystallize it, to give a colorless and needle crystal (yield 16.6 g, 75.5 mmol, recovery: 27.2%).

m.p.;145–148° C. $[\alpha]_D$=+172.2° (c 0.97, $CHCl_3$)

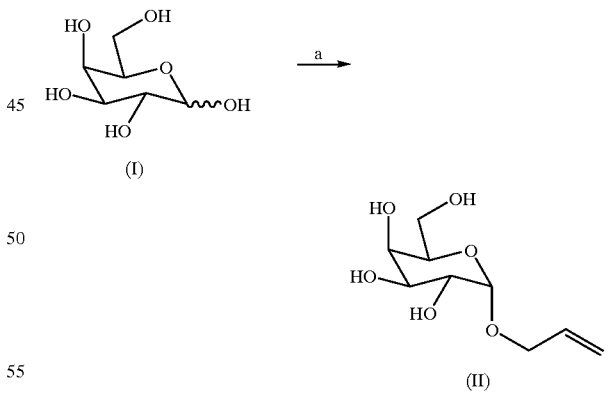

Route b: 1-O-(2-propenyl)-6-O-triphenylmethyl-α-D-galactose (III)

The Compound (II)(11.1 g, 50.2 mmol) was dissolved in 50 mL of anhydrous pyridine. To the solution, 16.8 g (60.2 mmol) of tritylchloride and 614 mg (5.02 mmol) of p-dimethylaminopyridine (DMAP) were added. The mixture was allowed to react for 24 hours at 40° C. while stirring. Then, the reaction was quenched by addition of 100 mL of cold water, and then extracted with ethyl acetate (3×200 mL). The organic layers were combined, neutralized to pH 4 with 1.0N hydrochloric acid, washed with brine (2×200 mL), dried over anhydrous sodium sulfate, filtered, concentrated in vacuo, and purified by silica gel flash chromatography (chloroform: methanol=20:1→15:1) to give a pale yellowish oily substance (yield:21.3 g, 46.1 mmol, recovery 91.8%).

$[\alpha]_D$=+64.2° (c 1.48, CHCl$_3$)

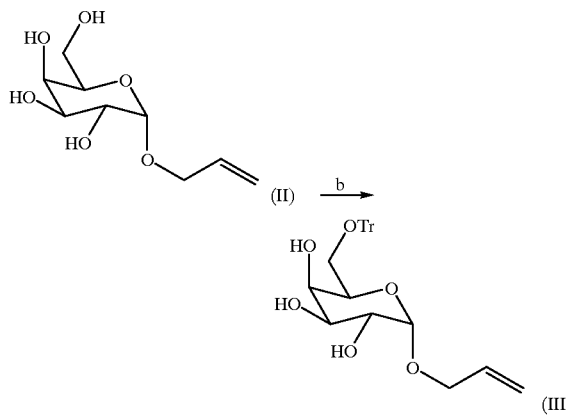

Route c: 2,3,4-tri-O-benzyl-1-O-(2-propenyl)-6-O-triphenylmethyl-α-D-galactose (IV)

60% sodium hydride (1.81 g, 45.2 mmol) dispersed in a mineral oil was put into a reactor and sufficiently washed with 50 mL of anhydrous hexane.

Then, the hexane was removed from the reactor, to which 5.24 g (11.3 mmol) of the compound (III) dissolved in anhydrous N,N-dimethylformamide (40 mL) was slowly added under an ice-cooled condition. After 15 minutes, the reaction mixture was returned to room temperature, and reacted for 1 hour while stirring.

Next, 7.73 g (45.2 mmol) of benzyl bromide was slowly added to the reaction mixture under an ice-cooled condition again. After 15 minutes, the reaction mixture was returned to room temperature, and reacted for 4 hours while stirring. Then, 20 mL of methanol and 100 mL of cold water were added to the reaction mixture to quench the reaction. The reaction mixture was extracted with ethyl acetate (3×150 mL). The organic layers were combined, washed with brine (2×200 mL), dried over anhydrous sodium sulfate, filtered, concentrated in vacuo, and purified by silica gel flash chromatography (hexane : ethyl acetate=10:1) to give a colorless and needle crystal (yield: 5.97 g, 8.15 mmol, recovery: 72.1%)

m.p.; 117–119° C., $[\alpha]_D$=+32.0° (c 1.00, CHCl$_3$)

IR (CHCl$_3$, cm$^{-1}$); 3070 & 3010 (Ar), 1945 & 1860 & 1810 (monosubstituted Ar), 1640 (terminal double bond), 1595 & 1585 & 1490 (Ar), 1110–980 (CO), 900 & 840 (α-hexose)

$^1$H NMR (300 MHz, CDCl$_3$+TMS, δ); 7.41–7.08 (30H, m, Ar), 5.99–5.88 (1H, m, —C$\underline{H}$=CH$_2$), 5.31 (1H, d, J=17.2, —CH=C$\underline{H}_2$), 5.21 (1H, d, J=10.7,—CH=C$\underline{H}_2$), 4.87 (1H, d, J=12.3, Ar—C$\underline{H}_2$), 4.85 (1H, d, J=4.5, H-1), 4.82 (1H, d, J=11.9, Ar—C$\underline{H}_2$), 4.79 (1H, d, J=11.8, Ar—C$\underline{H}_2$), 4.72 (1H, d, J=11.8, Ar—C$\underline{H}_2$), 4.57 (1H, d, J=11.9, Ar—C$\underline{H}_2$), 4.46 (1H, d, J=11.3, Ar—C$\underline{H}_2$), 4.16 (1H, ddd, J=1.1 & 5.3 & 12.9,—O—C$\underline{H}_2$—CH=CH$_2$), 4.04 (1H, ddd, J=0.9 & 6.6 & 12.9,—O—C$\underline{H}_2$—CH=CH$_2$), 4.00–3.94 (2H, m, H-2 & H-3), 3.91 (1H, br s, H-4), 3.85 (1H, t, J=6.2, H-5), 3.40 (1H, dd, J=6.2 & 9.3, H-6 a), 3.11 (1H, dd, J=6.6 & 9.0, H-6 b)

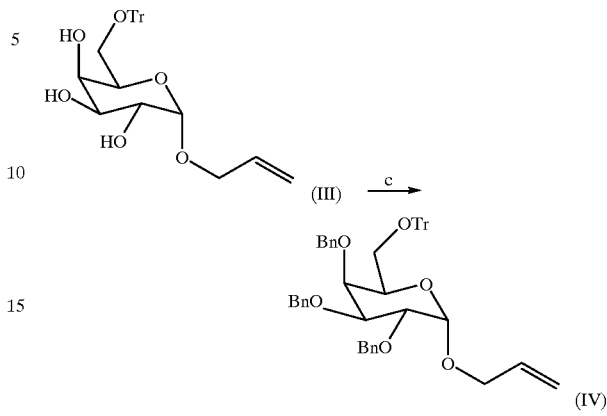

Route d: 2,3,4-tri-O-benzyl-1-O-(2-propenyl)-α-D-galactose(V)

Into 60 mL of a solution of acetic acid : methanol=1:1, 4.89 g (6.68 mmol) of the compound (IV) was suspended, and 1.27 g (6.68 mmol) of p-toluenesulfonic acid monohydrate was added to dissolve it while vigorously stirring (the reaction time: 1 hour). Then, the reaction was quenched by adding 100 mL of 5N cold aqueous solution of sodium hydroxide. The reaction mixture was extracted with ethyl acetate (3×200 mL). The organic layers were combined, washed with brine (2×200 mL), dried over anhydrous sodium sulfate, filtered, concentrated in vacuo, and purified by silica gel flash chromatography (hexane : ethyl acetate= 6:1→4:1→2:1) to give a colorless and transparent oily substance (3.11 g, 6.34 mmol, recovery: 94.4%).

$[\alpha]_D$=+23.0° (c 1.13, CHCl$_3$)

IR (CHCl$_3$, cm$^{-1}$);3400 (OH), 3070 & 3000 (Ar), 1950 & 1870 & 1810 (monosubstituted Ar), 1630 (terminal double bond), 1585 & 1495 (Ar), 1140–980 (CO), 910 & 830 (α-hexose)

$^1$H NMR (300 MHz, CDCl$_3$+TMS, δ); 7.63–7.24 (15H, m, Ar), 5.93–5.87 (1H, m, —C$\underline{H}$=CH$_2$), 5.30 (1H, d, J=17.2, —CH=C$\underline{H}_2$), 5.20 (1H, d, J=10.3,—CH=C$\underline{H}_2$), 4.98 (1H, d, J=11.6, Ar—C$\underline{H}_2$), 4.91 (1H, d, J=3.5, H-1), 4.91 (1H, d, J=11.6, Ar—C$\underline{H}_2$), 4.83 (1H, d, J=12.0, Ar—C$\underline{H}_2$), 4.76 (1H, d, J=11.7, Ar—C$\underline{H}_2$), 4.68 (1H, d, J=12.9, Ar—C$\underline{H}_2$), 4.64 (1H, d, J=11.9, Ar—C$\underline{H}_2$), 4.17–3.96 (4H, m, H-2 & H-3 & —O—C$\underline{H}_2$—CH=CH$_2$), 3.96 (1H, br s, H-4), 3.79 (1H, t, J=5.7, H-5), 3.70 (1H, dd, J=11.0 & 6.4, H-6 a), 3.49 (1H, br, H-6 b)

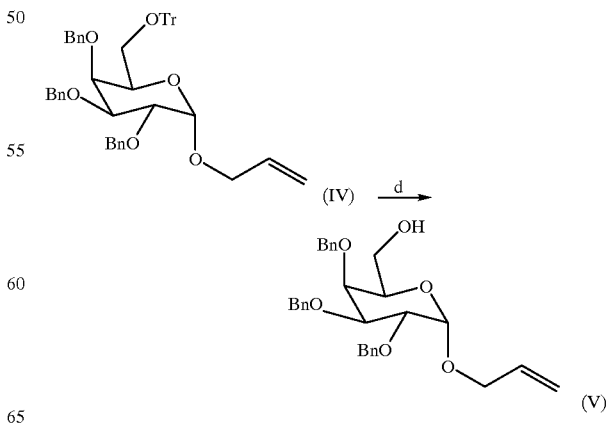

Route e: 2,3,4-tri-O-benzyl-1-O-(2-propenyl)-6-O-(4-tolylsulfonyl)-α-D-galactose (VI)

Into 50 mL of anhydrous pyridine, 3.06 g (6.25 mmol) of the compound (V) was dissolved, and then 76.4 mg (625 μmol) of DMAP and 1.79 g (9.38 mmol) of p-toluenesulfonyl chloride were added. The solution was reacted overnight at room temperature while stirring. Then, the reaction was quenched by adding 200 mL of cold water, and the reaction mixture was extracted with ethyl acetate (3×200 mL). The resultant organic layers were combined, neutralized to pH 4 with 1.0N and 0.1N hydrochloric acid, washed with brine (2×200 mL), dried over anhydrous sodium sulfate, filtered, concentrated in vacuo, and purified by silica gel flash chromatography (hexane : ethyl acetate= 4:1) to give a colorless and transparent oily substance (yield: 3.78 g, 5.88 mmol, yield: 94.1%).

$[\alpha]_D$=+35.2° (c 1.05, CHCl$_3$)

IR (CHCl$_3$, cm$^{-1}$);3070 & 3010 (Ar), 1950 & 1870 & 1800 (monosubstituted Ar), 1640 (terminal double bond), 1595 & 1495 (Ar), 1150–950 (CO), 950 & 850(α-hexose)

$^1$H NMR (300 MHz, CDCl$_3$+TMS, δ); 7.72 (2H, d, J=8.3, H at Ts Me), 7.37–7.24 (15H, m, Ar), 7.19–7.16 (2H, m, H at Ts SO$_2$), 5.93–5.82 (1H, m, —CH=CH$_2$), 5.28 (1H, dd, J=1.5 & 17.2,—CH=CH$_2$), 5.19 (1H, dd, J=1.2 & 10.3,—CH=CH$_2$), 4.92 (1H, d, J=11.3, Ar—CH$_2$), 4.86 (1H, d, J=11.7, Ar—CH$_2$), 4.80 (1H, d, J=2.9, H-1), 4.78 (1H, d, J=11.8, Ar—CH$_2$), 4.75 (1H, d, J=11.7, Ar—CH$_2$), 4.64 (1H, d, J=12.0, Ar—CH$_2$), 4.45 (1H, d, J=11.3, Ar—CH$_2$), 4.10–3.86 (8H, m, —O—CH$_2$—CH=CH$_2$ & H-2 & H-3 & H-4 & H-5 & H-6 a, b), 2.41 (3H, s, Ts CH$_3$)

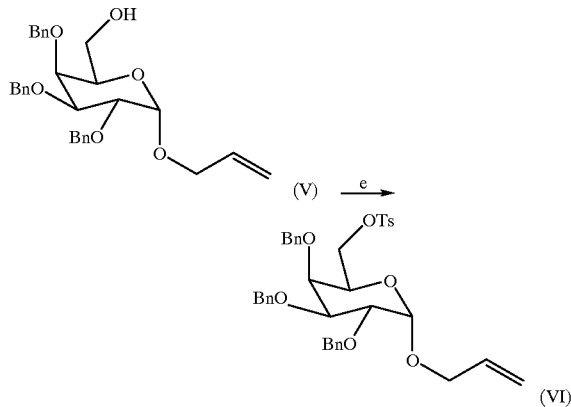

Route f; 2,3,4-tri-O-benzyl-1-O-(2-propenyl)-6-deoxy-6-acetylthio-α-D-galactose (VII)

Into 24 mL of hexamethylphosphoramide, 3.10 g (5.66 mmol) of the compound (VI) was dissolved and then 1.29 g (11.3 mmol) of potassium thioacetate was added. The solution was reacted in an oil bath at 100–110° C. for 3 hours while stirring. Thereafter, the reaction was quenched by adding 100 mL of cold water, and the reaction mixture was extracted with ethyl acetate (3×150 mL). The organic layers were combined, washed with brine (2×200 mL), dried over anhydrous sodium sulfate, filtered, concentrated in vacuo, and purified by silica gel flash chromatography (hexane : ethyl acetate=10:1→8:1) to give a brown and oily substance (yield: 2.42 g, 4.41 mmol, recovery: 77.9%)

$[\alpha]_D$=+36.8° (c 0.95, CHCl$_3$)

IR (CHCl$_3$, cm$^{-1}$); 3050 & 3010 (Ar), 1940 & 1860 & 1800 (monosubstituted Ar), 1670 (SCOCH$_3$), 1595 & 1575 & 1495 (Ar), 1150–900 (CO), 840 (α-hexose)

$^1$H NMR (300 MHz, CDCl$_3$+TMS, δ); 7.56–7.22 (15H, m, Ar), 5.91 (1H, m, —CH=CH$_2$), 5.30 (1H, d, J=17.2, —CH=CH$_2$), 5.20 (1H, d, J=10.3,—CH=CH$_2$), 5.03–4.59 (7H, m, Ar—CH$_2$ & H-1), 4.19–4.13 (1H, m, —O—CH$_2$—CH=CH$_2$), 4.07–3.92 (3H, m, —O—CH$_2$—CH=CH$_2$ & H-2 & H-3), 3.89 (1H, br S, H-4), 3.76–3.71 (1H, m, H-5), 3.02–2.97 (2H, m, H-6 a, b), 2.29 (3H, s, SCOCH$_3$)

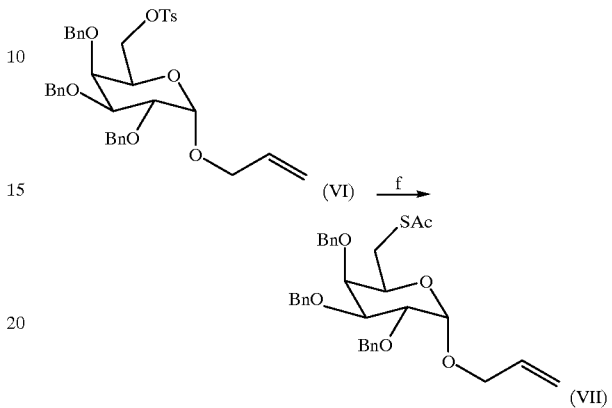

Route g; 3-O-(2,3,4-tri-O-benzyl-6-deoxy-6-acetylthio-α-D-galactopyranosyl)-glycerol (VIII)

Into 20 mL of a mixture of t-butanol : water (=4:1), 2.36 g (4.31 mmol) of the compound (VII) was dissolved and then 1.08 g (9.48 mmol) of trimethylamine N-oxide dihydrate and 5 mL of 0.05 M solution of osmium tetraoxide in t-butanol were added. The solution was reacted at room temperature for 24 hours while stirring. Thereafter, 2 g of activated charcoal was added, and the reaction mixture was allowed to stand at room temperature for 1 hour while stirring to adsorb the osmium tetraoxide. After filtration with suction, the reaction was quenched by adding 300 mL of cold water, and extracted with ethyl acetate (3×200 ml). The organic layers were combined, washed with brine (2×200 mL), dried over anhydrous sodium sulfate, filtered, concentrated in vacuo, and purified by silica gel flash chromatography (hexane : ethyl acetate=1:1) to give a pale brown oily substance (yield: 2.22g, 3.81 mmol, yield: 88.3%)

IR (CHCl$_3$, cm$^{-1}$);3300 (OH), 3060 & 3020 (Ar), 1950 & 1870 & 1810 (monosubstituted Ar), 1670 (SCOCH$_3$), 1600 & 1580 & 1495 (Ar), 1100–940 (CO), 910 & 850(α-hexose)

$^1$H NMR (300 MHz, CDCl$_3$+TMS, δ); 7.41–7.24 (15H, m, Ar), 5.00 (1H, d, J=11.4, Ar—CH$_2$), 4.84–4.67 (4H, m, Ar—CH$_2$ & H-1), 4.65 (1H, d, J=11.9, Ar—CH$_2$), 4.60 (1H, d, J=11.4, Ar—CH$_2$), 4.05–3.39(9H, m, Gly-1a,b & Gly-2 & Gly-3a,b & H-2 & H-3 & H-4 & H-5) 3.03 (1H, dd, J=7.6 & 13.7, H-6 a), 2.93 (1H, ddd, J=1.2 & 5.8 & 13.5, H-6 b), 2.30 (3H, s, SCOCH$_3$)

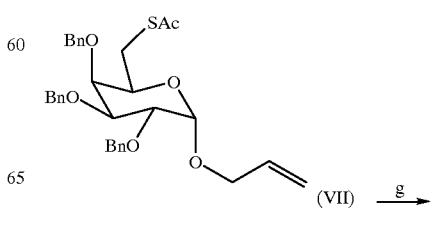

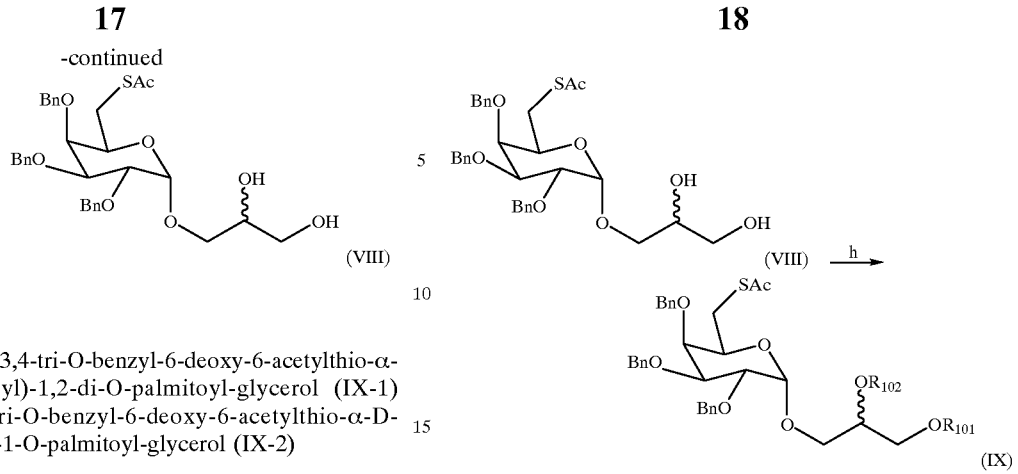

(IX-1; R<sub>101</sub> = R<sub>102</sub> = palmitoyl:
IX-2; R<sub>101</sub> = palmitoyl, R<sub>102</sub> = H Route h; 3-O-(2,3,4-tri-O-benzyl-6-deoxy-6-acetylthio-α-D-galactopyranosyl)-1,2-di-O-palmitoyl-glycerol (IX-1) and 3-O-(2,3,4-tri-O-benzyl-6-deoxy-6-acetylthio-α-D-galactopyranosyl)-1-O-palmitoyl-glycerol (IX-2)

Into 30 mL of anhydrous dichloromethane, 558 mg (958 μmol) of the compound (VIII) was dissolved and then 312 mg (1.63 mmol) of 1-ethyl-3-(3-dimethylaminopropyl)-carbodiimide hydrochloride, 11.7 mg (95.8 μmol) of DMAP, and 368 mg (1.44 mmol) of palmitic acid were added. The solution was reacted at room temperature for 3 hours while stirring. Then, the reaction was quenched by adding 100 mL of dichloromethane, and washed with brine (1×100 mL), dried over anhydrous sodium sulfate, filtered, concentrated in vacuo, and purified by silica gel flash chromatography (hexane : ethyl acetate=10:1→4:1 →2:1) (yield of the diester: 340 mg (321 μmol) and yield of the monoester: 468 mg (571 μmol); recovery (both esters in total): 93.1%).

Diester; whitish oily substance $[\alpha]_D = +24.5°$ (c 0.94, CHCl$_3$)

IR (CHCl$_3$, cm$^{-1}$);1730 (OCOCH$_2$), 1680 (SCOCH$_3$), 1495 (Ar), 1135–1020 (CO), 905 & 835 (α-hexose)

$^1$H NMR (300 MHz, CDCl$_3$+TMS, δ); 7.40–7.24 (15H, m, Ar), 5.28–5.23 (1H, m, Gly-2), 5.00 (1H, d, J=11.4, Ar—CH$_2$), 4.88–4.72 (4H, m, Ar—CH$_2$ & H-1), 4.67–4.59 (2H, m, Ar—CH$_2$), 4.39–4.32 (1H, m, Gly-1 a), 4.23–4.14 (1H, m, Gly-1 b), 4.04–3.99 (1H, m, H-2), 3.89–3.87 (2H, m, H-3 & H-4), 3.80–3.72 (1H, m, Gly-1a), 3.67 (1H, t, J=6.7, H-5), 3.58–3.48 (1H, m, Gly-1b), 3.07–2.91 (2H, m, H-6 a, b), 2.36–2.24 (7H, m, SCOCH$_3$ & OCOCH$_2$), 1.62–1.58 (4H, m, OCOCH$_2$CH$_2$), 1.25 (48H, br, —CH$_2$—), 0.86 (6H, t, J=6.4, CH$_3$)

Monoester; Colorless and transparent oily substance.

$[\alpha]_D = +32.9°$ (c 0.96, CHCl$_3$)

IR (CHCl$_3$, cm$^{-1}$);3400 (OH), 1730 (OCOCH$_2$), 1690 (SCOCH$_3$), 1490 (Ar), 1160–970 (CO), 910 & 840 (αhexose)

$^1$H NMR (300 MHz, CDCl$_3$+TMS, δ); 7.41–7.25 (15H, m, Ar), 5.01 (1H, d, J=11.3, Ar—CH$_2$), 4.86–4.64 (5H, m, Ar—CH$_2$ & H-1), 4.61 (1H, d, J=11.4, Ar—CH$_2$), 4.18–3.40 (9H, m, Gly-1a,b & Gly-2 & Gly-3a,b & H-2 & H-3 & H-4 & H-5), 3.07–2.90 (2H, m, H-6 a, b), 2.36–2.31 (5H, m, SCOCH$_3$ & OCOCH$_2$), 1.64–1.58 (2H, m, OCOCH$_2$CH$_2$), 1.25 (24H, br, —CH$_2$—), 0.88 (3H, t, J=6.2, CH$_3$)

Route i-i: 3-O-(2,3,4-tri-O-benzyl-6-deoxy-6-sulfo-α-D-galactopyranosyl)-1,2-di-O-palmitoyl-glycerol sodium salt (X-1)

Into 20 mL of acetic acid, 303 mg (286 μmol) of the compound (IX-1) was dissolved and then 500 mg of potassium acetate and 527 mg of OXONE (2KHSO$_5$, KHSO$_4$, K$_2$SO$_4$) were added. The solution was reacted at room temperature overnight while stirring. Thereafter, the reaction was quenched by adding 100 mL of 3N cold aqueous solution of sodium hydroxide, extracted with ethyl acetate (3×100 mL). The organic layers were combined, neutralized with saturated sodium hydrogencarbonate solution (1×50 mL), washed with brine (2×100 mL), dried over anhydrous sodium sulfate, filtered, concentrated in vacuo, and purified by silica gel flash chromatography (chloroform 100%→chloroform:methanol=10:1) to give a colorless and transparent oily substance (yield: 257 mg, 237 μmol, recovery: 82.9%)

$[\alpha]_D = +48.5°$ (c 1.01, CHCl$_3$)

IR (CHCl$_3$, cm$^{-1}$);1720 (OCOCH$_2$), 1490 (Ar), 1160–990 (CO)

$^1$H NMR (300 MHz, CDCl$_3$+TMS, δ); 7.25 (15H, m, Ar), 5.25 (1H, br, Gly-2), 4.91–2.96 (4H, br m, Ar—CH$_2$ & H-1 & Gly-1 a, b & Gly-3 a, b & H-2 & H-3 & H-4 & H-5 & H-6a, b), 2.21–2.18 (4H, br, OCOCH$_2$), 1.49 (4H, br, OCOCH$_2$CH$_2$), 1.25 (48H, br, —CH$_2$—), 0.88 (6H, t, J=6.5, CH$_3$)

Route i-2:3-O-(2,3,4-tri-O-benzyl-6-deoxy-6-sulfo-α-D-galactopyranosyl)-1-O-palmitoyl-glycerol sodium salt (X-2)

Into 20 mL of acetic acid, 430 mg (524 μmol) of the compound (IX-2) was dissolved and then 500 mg of potassium acetate and 966 mg of OXONE (2KHSO$_5$, KHSO$_4$, K$_2$SO$_4$) were added. The solution was reacted at room temperature overnight while stirring. Thereafter, the reaction was quenched by adding 100 mL of 3N cold aqueous solution of sodium hydroxide, extracted with ethyl acetate (3×100 mL). The organic layers were combined, neutralized with saturated sodium hydrogencarbonate solution (1×50 mL), washed with brine (2×100 mL), dried over anhydrous sodium sulfate, filtered, concentrated in vacuo, and purified by silica gel flash chromatography (chlorohofrm 100%→chloroform:methanol=5:1) to give a colorless and transparent oily substance (yield: 442 mg, 521 μmol, recovery: 99.4%).

$[\alpha]_D = +57.3°$ (c 0.89, CHCl$_3$)

IR (CHCl$_3$, cm$^{-1}$);3400 (OH), 1720 (OCOCH$_2$), 1490 (Ar), 1200–1020 (CO).

$^1$H NMR (300 MHz, CDCl$_3$+TMS, δ); 7.29–7.22 (15H, br, Ar), 4.90–4.45 (7H, br m, Ar—CH$_2$ & H-1), 4.13–3.58

(9H, br m, Gly-1 a, b & Gly-2 & Gly-3a, b & H-2 & H-3 & H-4 & H-5), 3.38 (1H, br, H-6a), 3.08 (2H, br, H-6 a), 2.16 (2H, br, OCOC$\underline{H}_2$), 1.45 (2H, br, OCOCH$_2$C$\underline{H}_2$), 1.24 (24H, br, —CH$_2$—), 0.88 (3H, t, J=6.5, CH$_3$)

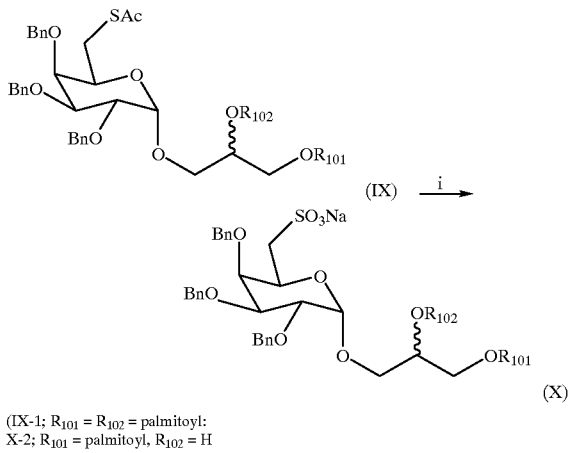

(IX-1; R$_{101}$ = R$_{102}$ = palmitoyl:
X-2; R$_{101}$ = palmitoyl, R$_{102}$ = H Route j-1:3-O-(6-deoxy-6-sulfo-α-D-galactopyranosyl)-1,2-di-O-palmitoyl-glycerol sodium salt (XI-1)

Into 20 mL of ethanol, 227 mg (209 μmol) of the compound (X-1) was dissolved and 1.00 g of 10% palladium-activated carbon (Pd—C) was added. The inner atmosphere of a flask was replaced with hydrogen and the solution was reacted at room temperature overnight while stirring. The reaction solution was filtered with suction, concentrated in vacuo, and purified by silica gel flash chromatography (chloroform: methanol 10:1→7:3 chloroform:methanol:water=70:30:4) to give a white amorphous solid substance (yield: 111 mg, 136 μmol, recovery: 65.1%).

$^1$H NMR (300 MHz, CDCl$_3$+CD$_3$OD+D$_2$O+TMS, δ); 5.30–5.28 (1H, m, Gly-2), 4.83 (1H, d, J=3.3, H-1), 4.36–4.11 (3H, m, Gly-3a,b & H-2), 4.05 (1H, br s, H-4), 3.98–3.90 (1H, m, H-3), 3.82–3.78 (1H, m, Gly-1a), 3.75–3.71 (1H, m, Gly-3b), 3.65–3.55 (1H, m, H-5) 3.22 (1H, dd, J=6.6 & 13.9, H-6 a), 3.10–3.06 (1H, m, H-6 b), 2.37–2.29 (4H, m, OCOC$\underline{H}_2$), 1.59 (4H, br, OCOCH$_2$C$\underline{H}_2$), 1.26 (48H, br, —C$\underline{H}_2$—), 0.88 (6H, t, J=6.7, C$\underline{H}_3$)

Route j-2:3-O-(6-deoxy-6-sulfo-α-D-galactopyranosyl)-1-O-palmitoyl-glycerol sodium salt (XI-2)

Into 20 mL of ethanol, 442 mg (521 μmol) of the compound (X-2) was dissolved and 1.00 g of 10% Pd—C was added. The inner atmosphere of a flask was replaced with hydrogen and the solution was reacted at room temperature overnight while stirring. The reaction solution was filtered with suction, concentrated in vacuo, and purified by silica gel flash chromatography (chloroform: methanol= 10:1→7:3→chloroform: methanol:water=70:30:4) to give a white amorphous solid substance(yield: 270 mg, 467 μmol, recovery: 89.6%).

[α]$_D$=+57.6° (c 0.59, CH$_3$OH)

$^1$H NMR (300 MHz, CD$_3$OD, δ);4.70 (1H, d, J=2.2, H-1), 4.21–4.12 (1H, m, Gly-3 a), 4.09–4.04 (1H, m, Gly-3 b), 4.00–3.96 (1H, m, H-2), 3.87–3.84 (2H, m, H-3 & H-4), 3.71–3.57 (2H, m, Gly-1a,b), 3.30–3.23 (1H, m, H-5), 3.10–3.01 (1H, m, H-6 a), 2.99–2.90 (1H, m, H-6 b), 2.38–2.23 (2H, m, OCOC$\underline{H}_2$), 1.52–1.47 (2H, m, OCOCH$_2$C$\underline{H}_2$), 1.30 (24H, br, —C$\underline{H}_2$—), 0.78 (3H, t, J=6.5,

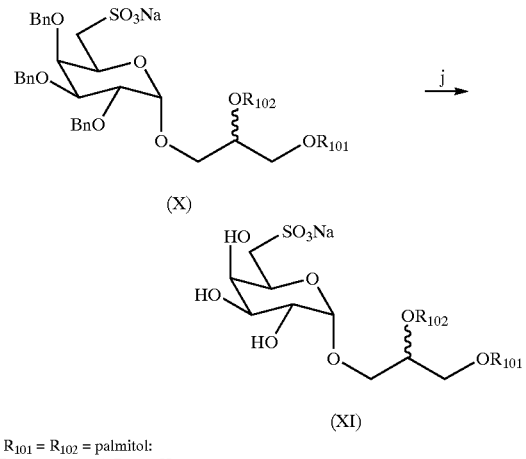

(XI-1, R$_{101}$ = R$_{102}$ = palmitol:
XI-2; R$_{101}$ = palmitoyl, R$_{102}$ = H

Example 2

Steps h–j were carried out in the same manner as in Example 1 except that myristic acid was used in place of palmitic acid in Step h of Example 1, to synthesize 3-O-(6-deoxy-6-sulfo-α-D-galactopyranosyl)-1,2-di-O-myristoyl-glycerol sodium salt and 3-O-(6-deoxy-6-sulfo-α-D-galactopyranosyl)-1-O-myristoyl-glycerol sodium salt.

Diester (yield: 82.7 mg, 109 μmol, recovery 64.5%), colorless and transparent oily substance.

Monoester (yield: 191 mg, 374 μmol, recovery 73.5%), colorless and transparent oily substance.

Example 3

Similar to Example 2, stearic acid was used in place of palmitic acid to synthesize 3-O-(6-deoxy-6-sulfo-α-D-galactopyranosyl)-1,2-di-O-stearoyl-glycerol sodium salt and 3-O-(6-deoxy-6-sulfo-α-D-galactopyranosyl)-1-O-stearoyl-glycerol sodium salt.

Diester (yield: 188 mg, 215 μmol, recovery 87.8%), white amorphous solid substance.

Monoester (yield: 212 mg, 350 μmol, recovery 85.4%), colorless and transparent oily substance.

The compounds represented by General Formula (1) of the present invention were subjected to physiological assays.

<Assay 1>

An assay on inhibitory effect against a DNA polymerase α was carried out in the following manner.

0.05 U of a DNA polymerase α purified and isolated from a bovine thymus by an immunoaffinity column was mixed with each of test compounds, sulfofucosylacylglycerol (hereinafter, simply referred to as "SFAG") derivatives, namely, SFAG1, SFAG2, SFAG3, SFAG4, SFAG5, and SFAG6 (listed in Table 1 below) dissolved in DMSO. Each mixture was added with a buffer containing inorganic salts for the enzymatic reaction, [$^3$H]-labeled dTTP and compounds for reaction containing a template DNA strand, and incubated at 37° C. for 60 minutes.

After the enzymatic reaction was quenched, the resultant reaction product was fixed on a dedicated filter and subjected to measurement by a liquid scintillation counter. The amount of enzymatically incorporated dTTP was calculated as a radiation dose (cpm) of [$^3$H]. Note that, each of the sulfofucosylacylglycerol derivatives is a mixture of the S- and R-configurations with respect to an absolute configuration of the carbon of the 2-position of the glycerol moiety.

The results are shown as $IC_{50}$ in Table 1 below.

TABLE 1

Inhibitory effect on DNA polymerase α

Inhibitory activity against DNA polymerase

| Compound | $R_{101}$ | $R_{102}$ | $IC_{50}$ (μg/mL) |
|---|---|---|---|
| SFAG1 | $CH_3(CH_2)_{12}CO-$ | H | 4.2 |
| SFAG2 | $CH_3(CH_2)_{14}CO-$ | H | 5.0 |
| SFAG3 | $CH_3(CH_2)_{16}CO-$ | H | 5.0 |
| SFAG4 | $CH_3(CH_2)_{12}CO-$ | $CH_3(CH_2)_{12}CO-$ | 0.5 |
| SFAG5 | $CH_3(CH_2)_{14}CO-$ | $CH_3(CH_2)_{14}CO-$ | 0.45 |
| SFAG6 | $CH_3(CH_2)_{16}CO-$ | $CH_3(CH_2)_{16}CO-$ | 0.4 |

AS is clear from Table 1, each of the compounds subjected to the assay exhibits a significant inhibitory activity against the DNA polymerase α.

Colon cancer cells and gastric cancer cells used in the following two assays are only for the purpose of illustration of cancer cells for which the medicinally active agent of the present invention effectively works. Thus, theses assays do not intend to limit the cancer cells for which the medicament of the invention is effective. Examples of other cancer cells include those of esophageal cancer, gastric cancer, colon cancer, including those at colon and recta, thyroid cancer, bladder cancer, kidney cancer, prostatic cancer, malignant lymphoma, brain tumor, lung cancer, laryngeal cancer, pharyngeal cancer, hepatic cancer, gallbladder cancer, bile duct cancer, pancreas cancer, breast cancer, uterine cancer, ovarian cancer, vaginal cancer, leukemia, childhood cancer, skin cancer, osteosarcoma, tongue cancer, cancer of small intestine, penile cancer, urethral cancer, ureteral cancer, testicular cancer, thymoma and myeroma.

<Assay 2>

An assay on anticancer activity against cultured colon cancer cells was carried out in the following manner.

Colon cancer cells DLD-1 were maintained and subcultured in RPMI 1640 medium (containing 10% calf serum). Each of the test compounds (SFAG1 to SFAG3 shown in Table 1) was suspended and diluted in the medium, and then the cancer cells were cultivated together with the medium in a 96-well plate at $3 \times 10^3$ cells/well. After 48 hour cultivation, the MTT assay (Mosmann, T: Journal of Immunological Method, 65, 55–63 (1983)) was carried out to compare survival rates.

The results are shown as $IC_{50}$ in Table 2 below.

TABLE 2

| | Anticancer activity against colon cancer cells | | |
|---|---|---|---|
| Compound | SFAG1 | SFAG2 | SFAG3 |
| $IC_{50}$ (μg/mL) | 44 | 41.5 | 27.5 |

As is clear from Table 2, all of the test compounds had significant anticancer activities against the colon cancer cells.

<Assay 3>

An assay on anticancer activity against cultured gastric cancer cells was carried out in the same manner as in the Assay 2 except that gastric cancer cells NUGC-3 were used instead of the colon cancer cells DLD-1.

The results are shown as $IC_{50}$ in Table 3 below.

TABLE 3

| | Anticancer activity against gastric cancer cells | | |
|---|---|---|---|
| Compound | SFAG1 | SFAG2 | SFAG3 |
| $IC_{50}$ (μg/ml) | 44.3 | 41.7 | 30.3 |

As is clear from Table 3, the test compounds had significant anticancer activities against the gastric cancer cells.

As shown in Assays 2 and 3, it can be considered that each of the test compounds independently has an anticancer activity equal to or more than that of a mixture of the sulfoquinovosylacylglycerol derivatives disclosed by Sahara et al. (British journal of cancer, 75 (3), 324–332 (1997)) in the Prior Art.

INDUSTRIAL APPLICABILITY

As explained in the foregoing, according to the present invention, there are provided novel sulfofucosylacylglycerol derivatives represented by General formula (1).

According to the present invention, there are provided medicaments containing at least one compound selected from the group consisting of sulfofucosylacylglycerol derivatives represented by General Formula (1) and pharmaceutically acceptable salts thereof, as an active ingredient.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A sulfofucosylacylglycerol compound represented by formula (1):

(1)

wherein $R_{101}$ represents an acyl residue of a higher fatty acid, and $R_{102}$ represents a hydrogen atom or an acyl residue of a higher fatty acid, or a pharmaceutically acceptable salt thereof.

2. The sulfofucosylacylglycerol compound or a pharmaceutically acceptable salt thereof according to claim 1, wherein said $R_{101}$ of formula (1) is an acyl residue represented by formula:

$CH_3(CH_2)_nCO-$ wherein n is an integer of 12–24; and said $R_{102}$ represents a hydrogen atom or an acyl residue represented by formula:

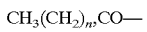

wherein n' is an integer of 12–24.

3. The sulfofucosylacylglycerol compound or a pharmaceutically acceptable salt thereof according to claim 2, wherein said $R_{102}$ of formula (1) is a hydrogen atom.

4. The sulfofucosylacylglycerol compound or a pharmaceutically acceptable salt thereof according to claim 3, wherein the bonding between sulfofucose and glycerol in formula (1) is in the α-configuration.

5. The sulfofucosylacylglycerol compound or a pharmaceutically acceptable salt thereof according to claim 4, wherein said $R_{101}$ of formula (1) is $CH_3(CH_2)_{12}CO-$.

6. The sulfofucosylacylglycerol compound or a pharmaceutically acceptable salt thereof according to claim 4, wherein said $R_{101}$ of formula (1) is $CH_3(CH_2)_{14}CO-$.

7. The sulfofucosylacylglycerol compound or a pharmaceutically acceptable salt thereof according to claim 4, wherein said $R_{101}$ of formula (1) is $CH_3(CH_2)_{16}CO-$.

8. The sulfofucosylacylglycerol compound or a pharmaceutically acceptable salt thereof according to claim 2, wherein said $R_{101}$ of formula (1) is an acyl residue represented by formula:

wherein n is an integer of 12–24; and said $R_{102}$ is an acyl residue represented by formula:

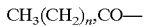

wherein n' is an integer of 12–24.

9. The sulfofucosylacylglycerol compound or a pharmaceutically acceptable salt thereof according to claim 8, wherein the bonding between sulfofucose and glycerol in formula (1) is in the α-configuration.

10. The sulfofucosylacylglycerol compound or a pharmaceutically acceptable salt thereof according to claim 9, wherein each of said $R_{101}$ and said $R_{102}$ of formula (1) is $CH_3(CH_2)_{12}CO-$.

11. The sulfofucosylacylglycerol compound or a pharmaceutically acceptable salt thereof according to claim 9, wherein each of said $R_{101}$ and said $R_{102}$ of formula (1) is $CH_3(CH_2)_{14}CO-$.

12. The sulfofucosylacylglycerol compound or a pharmaceutically acceptable salt thereof according to claim 9, wherein each of said $R_{101}$ and said $R_{102}$ of formula (1) is $CH_3(CH_2)_{16}CO-$.

13. A DNA polymerase inhibitor composition comprising:
   an effective DNA polymerase inhibiting amount of the compound represented by formula (1):

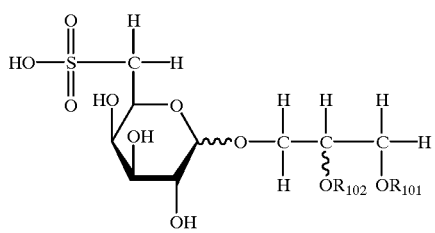

wherein $R_{101}$ represents an acyl residue of a higher fatty acid, and $R_{102}$ represents a hydrogen atom or an acyl residue of a higher fatty acid, and/or a pharmaceutically acceptable salt thereof; and
   a pharmaceutically acceptable excipient or diluent.

14. The DNA polymerase inhibitor composition according to claim 13, wherein said $R_{101}$ of formula (1) is an acyl residue represented by formula:

wherein n is an integer of 12–24; and said $R_{102}$ represents a hydrogen atom or an acyl residue represented by formula:

wherein n' is an integer of 12–24.

15. The DNA polymerase inhibitor composition according to claim 14, wherein said $R_{101}$ of formula (1) is a hydrogen atom.

16. The DNA polymerase inhibitor composition according to claim 15, wherein the bonding between sulfofucose and glycerol in formula (1) is in the α-configuration.

17. The DNA polymerase inhibitor composition according to claim 16, wherein said $R_{101}$ of formula (1) is $CH_3(CH_{12}CO-$.

18. The DNA polymerase inhibitor composition according to claim 16, wherein said $R_{101}$ of formula (1) is $CH_3(CH_2)_{14}CO-$.

19. The DNA polymerase inhibitor composition according to claim 16, wherein said $R_{101}$ of formula (1) is $CH_3(CH_2)_{16}CO-$.

20. The DNA polymerase inhibitor composition according to claim 14, wherein said $R_{101}$ of formula (1) is an acyl residue represented by formula:

wherein n is an integer of 12–24; and said $R_{102}$ is an acyl residue represented by formula:

wherein n' is an integer of 12–24.

21. The DNA polymerase inhibitor composition according to claim 20, wherein the bonding between sulfofucose and glycerol in formula (1) is in the α-configuration.

22. The DNA polymerase inhibitor composition according to claim 21, wherein each of said $R_{101}$ and said $R_{102}$ of formula (1) is $CH_3(CH_2)_{12}CO-$.

23. The DNA polymerase inhibitor composition according to claim 21, wherein each of said $R_{101}$ and said $R_{102}$ of formula (1) is $CH_3(CH_2)_{14}CO-$.

24. The DNA polymerase inhibitor composition according to claim 21, wherein each of said $R_{101}$ and said $R_{102}$ of formula (1) is $CH_3(CH_2)_{16}CO-$.

* * * * *

UNITED STATES PATENT AND TRADEMARK OFFICE
CERTIFICATE OF CORRECTION

| | | |
|---|---|---|
| PATENT NO. | : 6,740,640 B2 | |
| APPLICATION NO. | : 09/939153 | |
| DATED | : May 25, 2004 | |
| INVENTOR(S) | : Takayuki Yamazaki et al. | |

It is certified that error appears in the above-identified patent and that said Letters Patent is hereby corrected as shown below:

Please insert Item [56]

Title Page 1: Col. 1, Item (56) References Cited, under U.S. PATENT DOCUMENTS, insert
-- 09/939,338   Yamazaki et al. --;

Title Page 1: Col. 2, Item (56) References Cited, under OTHER PUBLICATIONS, line 16, replace "Methyll" with --Methyl--;

Title Page 2: Col. 2, line 25, after "from" delete "Byrsonima Crassifolia', Phytochemistry, 45, 647-650 (1997) ." and replace with
--Gracilaria Verrucosa", Phytochemistry, 29, 307-309 (1990) . --;

Title Page 2: Col. 2, after line 25, the Byeng Wha Son citation and before line 27, the Shirahashi et al. citation, insert the following citation:
--Luca Rastrelli, "Glycolipids from Byrsonima Crassifolia", Phytochemistry, 45, 647-650 (1997) . --;

Title Page 2: Col. 2, line 10 from the bottom, delete "Toxicity" with --Cytotoxicity--;

UNITED STATES PATENT AND TRADEMARK OFFICE
CERTIFICATE OF CORRECTION

PATENT NO. : 6,740,640 B2
APPLICATION NO. : 09/939153
DATED : May 25, 2004
INVENTOR(S) : Takayuki Yamazaki et al.

It is certified that error appears in the above-identified patent and that said Letters Patent is hereby corrected as shown below:

Title Pate 2: Col. 2, line 3 from the bottom,
delete "6-β-" with -- 6S- --.

Signed and Sealed this

Eighteenth Day of July, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,740,640 B2 |
| APPLICATION NO. | : 09/939153 |
| DATED | : May 25, 2004 |
| INVENTOR(S) | : Takayuki Yamazaki et al. |

It is certified that error appears in the above-identified patent and that said Letters Patent is hereby corrected as shown below:

Please insert Item [56]

Title Page 1: Col. 1, Item (56) References Cited, under U.S. PATENT DOCUMENTS, insert
-- 09/939,338  Yamazaki et al. --;

Title Page 1: Col. 2, Item (56) References Cited, under OTHER PUBLICATIONS, line 16, replace "Methyll" with --Methyl--;

Title Page 2: Col. 2, line 25, after "from" delete "Byrsonima Crassifolia', Phytochemistry, 45, 647-650 (1997) ." and replace with
--Gracilaria Verrucosa", Phytochemistry, 29, 307-309 (1990) . --;

Title Page 2: Col. 2, after line 25, the Byeng Wha Son citation and before line 27, the Shirahashi et al. citation, insert the following citation:
--Luca Rastrelli, "Glycolipids from Byrsonima Crassifolia", Phytochemistry, 45, 647-650 (1997) . --;

Title Page 2: Col. 2, line 10 from the bottom, delete "Toxicity" with --Cytotoxicity--;

Title Page 2: Col. 2, line 3 from the bottom, delete "6-β-" with -- 6S- --.

Title Page 1: Col. 2, Item (56) References Cited, under OTHER PUBLICATIONS, line 28, after "Green" insert --Alga--;

Title Page 2: Col. 1, line 19 from the bottom, replace "Gyanobacterium" with --Cyanobacterium--;

Title Page 2: Col. 1, line 11 from the bottom, replace "Sulfoquinosyldiacylglycerol" with --Sulfoquinovosyldiacylglycerol--;

UNITED STATES PATENT AND TRADEMARK OFFICE
CERTIFICATE OF CORRECTION

PATENT NO. : 6,740,640 B2
APPLICATION NO. : 09/939153
DATED : May 25, 2004
INVENTOR(S) : Takayuki Yamazaki et al.

It is certified that error appears in the above-identified patent and that said Letters Patent is hereby corrected as shown below:

Title Page 2: Col. 2, line 9, replace "matsukage" with --Matsukage--;

Title Page 2: Col. 2, line 13, replace "Cyanobacterail" with --Cyanobacterial--;

This certificate supersedes Certificate of Correction issued July 18, 2006.

Signed and Sealed this

First Day of May, 2007

JON W. DUDAS
*Director of the United States Patent and Trademark Office*